April 16, 1968 W. E. SILVA Plant Pat. 2,805
PYRACANTHA PLANT
Filed Sept. 8, 1966
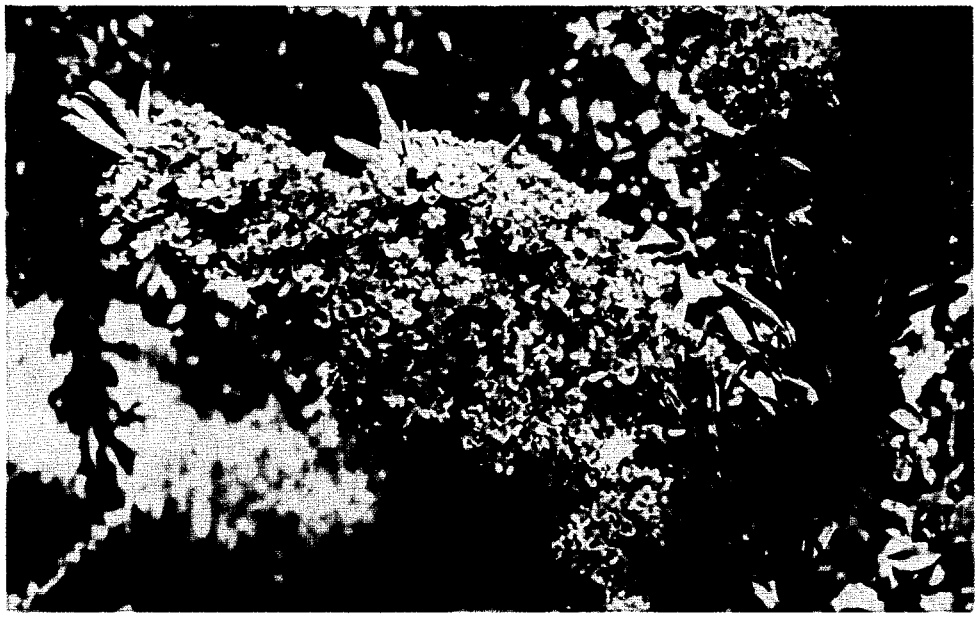
INVENTOR.
WILLIAM E. SILVA
BY J. F. Cuneo
ATTORNEY United States Patent Office Plant Pat. 2,805
Patented Apr. 16, 1968

2,805
PYRACANTHA PLANT

William E. Silva, Sebastopol, Calif., assignor to Select Nurseries, Brea, Calif., a corporation of California Filed Sept. 8, 1966, Ser. No. 578,105
1 Claim. (Cl. Plt.—54)

This invention relates to a new and distinct variety of hybrid shrub obtained by crossing a Pyracantha plant with a Cotoneaster plant that possesses especially attractive features as an ornamental shrub, and in particular to a new and distinct variety of hybrid shrub characterized by its profuse abundance of rose red flowers in the spring and red berries in the winter, by its long, narrow, dark green leaves, and by its substantially upright growth.

The new variety is classed as a bi-generic plant and was produced by me in 1958 at my growing grounds located at Sebastopol, Calif. This plant resulted from crossing *Pyracantha koidzumii* also known as *Pyracantha formosana,* an unpatented variety, as the seed parent, with *Cotoneaster acuminata,* also an unpatented variety originally from the Himalayas and known in the United States as *Cotoneaster grandiflora,* as the pollen parent. Care was always taken to prevent self pollenation or pollenation by other plants, and the following technique was adopted in breeding the new hybrid plant: a very small pair of tweezers with the aid of microscope were used to extract the anthers from the pollen parent, and extreme care was used not to injure the pistils when the pollen was applied to the stigmas. Before the pollen was used to impregnate the stigmas, the anthers were permitted to ripen in a small room for one or two days since these were usually taken from the pollen parent when they were almost ripe. The ripened pollen was then applied to the reactive stigma. The new variety bore the first flowers and berries in 1961, and the flowers had a rose red coloration. The plant has continued to produce these rose red flowers every year thereafter.

The new and distinct variety is readily distinguished from its seed parent in that the flowers of the seed parent are white while those of the new variety open up white with red spots and turn to a rose pink shortly after, becoming rose red when they are fully opened. The leaves of the new variety are dark green on the upper side and are longer and narrower than those of the seed parent. The new hybrid shrub differs from its pollen parent in that the pollen parent is a Cotoneaster, whereas the new hybrid shrub, with the exception of the rose red petals, retains predominantly the characteristics of the seed parent.

This new variety has been reproduced asexually in my growing grounds by means of cuttings. The distinguishing characteristics of the parent plant have been observed in all of the numerous asexually reproduced plants and show that the new variety appears to be well established. The new variety cannot be reproduced true from seed.

The following is a description of the plant, blooms, and berries. The names and numbers of the important colors included in this description are based on the nomenclature used in the Horticultural Colour Charts adopted by the British Colour Council.

*The plant*

Form: A vigorous upright shrub

Growth habit: The original plant is ten feet tall having a main trunk that at four feet branches out, the branches are very upright and give the plant a diameter of approximately two feet. The original plant is eight years old and in the Sebastopol area of California, its growth is classed as slow.

Foliage:

*Amount.*—Heavy.

*Size of leaves.*—The leaves are up to two inches in length and from one-quarter to five-sixteenths of an inch in width. These leaves are longer and narrower than those of most Pyracantha varieties.

*Color.*—Upper side—Ivy Green ooo1060/1. Under side—Spinach Green o960/3.

*Shape.*—The leaves are substantially spatulate with the apex of most leaves slightly emarginate. The base of the leaves is cuneate with the length of the taper being relatively long. The margin of the leaves is entire. The upper side of the leaves is slightly more shiny than the underside of the leaves which are classed as dull.

*Arrangement.*—The leaves grow on spurs on the main trunk on alternative spurs one-half inch apart, each group having from five to six leaves.

Stems: The stems of this variety are generally classed as coarse. Color—the stems are a dark brown.

Thorns: Each branch at the end of a spur has a thorn or prickle that is about one-quarter of an inch in length. The novel hybrid shrub has fewer and smaller thorns than its seed parent.

Resistance to fire blight: This variety has never shown signs of blight up to the present whereas other varieties of Pyracantha plants in close proximity to the new variety died from this disease.

*The bloom*

Blooming period: This variety is generally a late bloomer. In the coastal region of southern California it blooms in the last part of April and more generally in May. The novel hybrid shrub blooms slightly later than its seed parent, however, this is dependent on the prevailing weather conditions in the area where the plant is being observed. Occasionally this new hybrid shrub will puot out three or four clumps of flowers late in the summer or early in the fall, and these blooms are located at the end of the branches.

Arrangement: The flowers appear in clusters with several clusters grouped together. There are generally twenty-five to thirty blooms in a cluster and this is approximately the same number that is found in the clusters of the seed parent.

Petals: The petals are arranged in groups of five to form a five pointed star on one calyx.

*Size.*—Two mm. in length and three mm. in width.

*Color.*—On opening—petals are white with red spots. Just after opening—petals are China Rose o24/3. Fully mature—China Rose o24/1. The period elapsing from the time the white flowers with red spots appear until the flowers attain their fully matured color is usually from six to seven days. When the flowers begin to dry up they turn a brownish red.

Stamens: Each flower has approximately twenty stamens and the color of the stamens is lemon yellow.

Pistils: The pistils are short, brownish in color, and are very tiny, making them very difficult to see. The number of pistils appears to be one for each flower.

*The berries*

Texture: The mature berries are generally pithy and are relatively dry. Each berry contains five elongated seeds.

Size: The berries are medium size, varying from five-sixteenths to three-eighths inches in diameter.

Color: The mature berries are approximately Signal Red 719/1. The color of the berries resembles that of the berries of the seed parent.

Quantity: The berries are very abundant.

Arrangement: The berries form around the branches in clusters that are approximately two and one-half inches in diameter and are often as long as fourteen inches.

Persistence: The berries remain on the branches throughout winter.

Shape: The berries are round with both ends flattened.

I claim:

The new an distinct variety of hybrid shrub substantially as herein shown and described, characterized particularly as to novelty by its profuse abundance of rose red flowers which open up white with red spots, turn rose pink shortly after opening, and become rose red when fully opened; by its profuse abundance of red berries in the winter; by its very upright growth; and by its long, narrow, dark green leaves.

No references cited.

ROBERT E. BAGWILL, *Primary Examiner.*